United States Patent
Fehre et al.

(10) Patent No.: US 10,588,584 B2
(45) Date of Patent: Mar. 17, 2020

(54) MOBILE C-ARM X-RAY APPARATUS

(71) Applicant: SIEMENS HEALTHCARE GMBH, Erlangen (DE)

(72) Inventors: Jens Fehre, Hausen (DE); Ralf Nanke, Neunkirchen am Brand (DE)

(73) Assignee: Siemens Healthcare GmbH, Erlangen (DE)

( * ) Notice: Subject to any disclaimer, the term of this patent is extended or adjusted under 35 U.S.C. 154(b) by 119 days.

(21) Appl. No.: 15/764,075

(22) PCT Filed: Aug. 9, 2016

(86) PCT No.: PCT/EP2016/068924
§ 371 (c)(1),
(2) Date: Mar. 28, 2018

(87) PCT Pub. No.: WO2017/054974
PCT Pub. Date: Apr. 6, 2017

(65) Prior Publication Data
US 2018/0317870 A1    Nov. 8, 2018

(30) Foreign Application Priority Data
Sep. 30, 2015 (DE) .................. 10 2015 218 919

(51) Int. Cl.
*H01M 10/0525* (2010.01)
*A61B 6/00* (2006.01)
(Continued)

(52) U.S. Cl.
CPC .......... *A61B 6/4405* (2013.01); *A61B 6/4441* (2013.01); *A61B 6/548* (2013.01);
(Continued)

(58) Field of Classification Search
CPC ..... A61B 6/4405; A61B 6/4441; A61B 6/508; A61B 6/54; H05G 1/32; H01M 10/052; H01M 10/0525; H01M 2220/20
See application file for complete search history.

(56) References Cited

U.S. PATENT DOCUMENTS

| 4,797,907 A | 1/1989 | Anderton |
|---|---|---|
| 6,169,782 B1 | 1/2001 | Zetterlund |

(Continued)

FOREIGN PATENT DOCUMENTS

| DE | 69900767 T2 | 8/2002 |
|---|---|---|
| DE | 102011050285 A1 | 11/2011 |

(Continued)

OTHER PUBLICATIONS

Jens Fehre et al. "Energiespeichereinheit als schnell aufladbare Speicherbatterie für motorisch unterstützte Gerätebewegungen von mobilen Röntgengeräten" ("Energy storage unit as a rechargeable storage battery for motor-assisted device movements of mobile X-ray devices") (machine translation included).

(Continued)

*Primary Examiner* — David P Porta
*Assistant Examiner* — Fani Boosalis
(74) *Attorney, Agent, or Firm* — Lempia Summerfield Katz LLC (57) ABSTRACT

A mobile c-arm X-ray apparatus is described. The mobile X-ray apparatus includes an electrically operated X-ray source. The mobile C-arm X-ray apparatus also includes an electrical energy storage device having a high current-capable accumulator. The electrical energy storage device includes a first electrical terminal electrically connected to the electrically operated X-ray source and a second electrical terminal used by a system energy supply. A method for operating the mobile X-ray apparatus is also described.

14 Claims, 3 Drawing Sheets

(51) Int. Cl.
  *H01M 10/052*   (2010.01)
  *H05G 1/10*     (2006.01)
  *H05G 1/32*     (2006.01)

(52) U.S. Cl.
  CPC ...... *H01M 10/0525* (2013.01); *H01M 10/052* (2013.01); *H01M 2220/20* (2013.01); *H05G 1/10* (2013.01); *H05G 1/32* (2013.01); *Y02E 60/122* (2013.01)

(56) References Cited

U.S. PATENT DOCUMENTS

| | | |
|---|---|---|
| 2006/0034427 A1 | 2/2006 | Brooks |
| 2008/0123818 A1 | 5/2008 | Alder et al. |
| 2008/0170666 A1 | 7/2008 | Coombs |
| 2010/0299014 A1* | 11/2010 | Bouvier ............... A61B 6/4405 701/25 |
| 2011/0286575 A1 | 11/2011 | Omernick et al. |
| 2012/0133339 A1 | 5/2012 | Eguchi |
| 2014/0016747 A1 | 1/2014 | Watanabe |

FOREIGN PATENT DOCUMENTS

| | | |
|---|---|---|
| EP | 2380496 A1 | 10/2011 |
| EP | 2422701 A1 | 2/2012 |
| WO | 2008057713 A2 | 5/2008 |

OTHER PUBLICATIONS

Tesla Motors. http://www.teslamotors.com/supercharger; retrieved Mar. 28, 2018 (machine translation included).
Wikipedia Tesla Gigafactory. https://en.wikipedia.org/wiki/Tesla_Gigafactory; retrieved Mar. 28, 2018.
PCT International Search Report and Written Opinion of the International Searching Authority dated Oct. 25, 2016, for corresponding PCT/EP2016068924.

* cited by examiner

MOBILE C-ARM X-RAY APPARATUS

CROSS-REFERENCE TO RELATED APPLICATIONS

This application is the National Stage of International Application No. PCT/EP2016/068924, filed Aug. 9, 2016, which claims the benefit of German Patent Application No. DE 102015218919.8, filed Sep. 30, 2015. The entire contents of these documents are hereby incorporated herein by reference.

TECHNICAL FIELD

The present embodiments relate to a mobile C-arm X-ray apparatus and to a method for operating a mobile C-arm X-ray apparatus.

BACKGROUND

Medical imaging X-ray apparatuses are often used in hospitals as an aid for obtaining information for making a diagnosis. With the X-ray apparatuses, a shadow image of inside the body is created with the aid of X-rays that penetrate the body, as a function of the characteristics of the tissue of a region of the body that is to be examined.

For a flexible use of the X-ray apparatuses and increased economic efficiency, some X-ray apparatuses are constructed as mobile apparatuses. Such mobile apparatus may be used in common (e.g., by various units and departments) by the apparatus being moved between the individual facilities to locations where a radiological examination is about to be carried out. To provide traction for such a mobile X-ray apparatus and to supply power to the imaging system of such a mobile X-ray apparatus, lead-acid batteries are used. However, lead-acid batteries have the disadvantage of heavy weight and of a long charging time (e.g., from 5 to 7 hours). In intensive operation of an X-ray apparatus (e.g., in an operating theater), long charging times are problematic.

When operating an X-ray apparatus, electric currents with high amperage are briefly required for the actual imaging in order to operate the X-ray source of the X-ray apparatus. Typical power consumptions of mobile X-ray sources are between 2 kW and 25 kW. The high currents required for the X-ray apparatus are not drawn from the normal single-phase household power supply. For this reason, X-ray apparatuses may include a condenser unit as a current storage facility. The condenser unit may provide short-term electrical energy that flows with sufficiently high power values to operate an X-ray source. However, such condenser units only have a very limited storage capacity and therefore constantly have to be charged again via the power network. The X-ray apparatus therefore has to be connected on site to an electrical energy supply by an electric cable. In confined areas of a hospital (e.g., as in operating theaters), such cable connections may be very obstructive or may even be a safety hazard.

For example, in the field of C-arm X-ray systems, completely autonomous apparatuses have not yet been used. C-arm X-ray systems are may be provided with electrical energy by a stationary power connection, and a condenser unit is used as buffer storage to power the X-ray source.

A C-arm X-ray apparatus with a condenser unit as an energy storage device for the X-ray source is described in Fehre, et al. "*Energiespeichereinheit als schnell aufladbare Speicherbatterie für motorisch unterstützte Gerätebewegungen von mobile Röntgengeräten*" [*Energy storage unit as a quick-chargeable storage battery for motor-assisted movements of X-ray mobile apparatuses*], IPAS Publication 2014J18453. Fehre, et al. disclose an autonomous C-arm X-ray apparatus with an energy storage device having a quick-chargeable high performance condenser unit to supply the drive and X-ray generation unit. Condensers only have a limited storage capacity, restricting the autonomous time of operation. Moreover, condensers are discharged via a discharge current that drops exponentially. When operated by electrical energy from the condensers, no constant operating current is supplied over time, necessitating a constant readjustment and complex power electronics.

SUMMARY AND DESCRIPTION

The scope of the present invention is defined solely by the appended claims and is not affected to any degree by the statements within this summary.

One or more of the present embodiments may obviate one or more of the drawbacks or limitations in the related art. For example, a mobile C-arm X-ray apparatus, and a method for operating a mobile C-arm X-ray apparatus, is provided as a flexibly useable C-arm X-ray system that may operate autonomously for longer times of operation.

The mobile C-arm X-ray apparatus according to an embodiment includes an electrically operated X-ray source. An X-ray source includes (e.g., as an X-ray tube to generate X-rays) an electron tube. In addition, the mobile C-arm X-ray apparatus also includes an electric energy storage device with a high current-capable battery. The high current-capable battery includes a first electrical terminal connected to the electrically operated X-ray source, and a second electrical terminal for providing a system power supply. A battery is to be understood as a rechargeable electric energy storage device (e.g., converting electrical energy into chemical energy and storing the chemical energy) When required, a battery converts the chemical energy back into electrical energy and provides the electrical energy to a consumer. A high current-capable battery is a battery that may provide the high currents needed for the short-term power requirements of X-ray sources. With an electric voltage of 400V and a power requirement of 25 kW, the amperage required may be 62.5 amperes. A system energy supply is to be understood as the supply of all the electronic and electrical units of the C-arm X-ray apparatus, except for the X-ray source.

C-arm X-ray apparatuses are often used to provide mobile medical imaging facilities in operating theaters. Due to the restricted space available, imaging apparatuses may be removed from the operating environment after imaging has been completed. In addition, power supply cables present an increased tripping hazard in such safety-sensitive areas, such as operating theaters. The mobile C-arm X-ray apparatus according to the present embodiments overcome these problems and may operate for a longer period completely autonomously and without any additional energy-supply cables.

In the method according to an embodiment for operating a mobile C-arm X-ray apparatus, the electrically operated X-ray source is supplied via the first terminal with electrical energy from the electric energy storage device that includes a high current-capable battery, and the system energy supply is provided via the second terminal of the electric energy storage device. The electric energy storage device provides both the power supply for the central function of the X-ray apparatus (e.g., generation of X-ray images) and for the system energy supply. The term system energy supply also includes supplying actuators of the C-arm X-ray apparatus with electric power. In general, an actuator is considered to be any type of unit that converts an electrical signal into a mechanical movement.

In an embodiment, the electric energy storage device of the mobile C-arm X-ray apparatus may have at least two energy storage regions. A first energy storage region is electrically connected to the first electrical terminal and a second energy storage region is electrically connected to the second electrical terminal. Supplying the X-ray source with electrical energy is achieved via the first energy storage region and supplying the other functional units (e.g., the actuators) with electrical energy is achieved via the second energy storage region. The first and the second energy storage regions may be configured to be dischargeable separately from each other. For example, if the X-ray source has discharged too much energy due to a long duration of the examination, only the first energy storage region may be completely discharged. The second energy storage region is not adversely affected by the discharge of electricity, such that the remaining functional units (e.g., the traction for the mobile C-arm X-ray apparatus) may continue to be supplied with energy by the second energy storage region. For example, when the first energy storage region fails, the mobility of the X-ray apparatus is not impaired. Furthermore, this also avoids the system from being suddenly being turned off during X-ray imaging due to a shortage of energy, with no further X-rays being stored in the system. Conversely, after the second energy storage region has been discharged, the mobile X-ray apparatus may still be moved by hand to the target destination, where the X-ray images may then be taken without being adversely affected by the discharge of the second energy storage region, and it is provided that power may be supplied via a cable connection to the other units that are combined under the term "system". In addition, the two energy storage units may be optimized for their fields of use independently of each other. For example, the first energy storage region may be optimized to a short-term high power output (e.g., for capturing X-ray images with short-term high power outputs, such as 25 kW) have to be achieved, wherein the total capacity of the first energy storage region may be configured to be low, because the operating time of the X-ray source is relatively short and the energy consumption of the X-ray source is comparatively slight over fairly long periods. On the other hand, the second energy storage region may best be optimized for a large amount of energy storage, whereas the power output of the second energy storage region may be set at lower values (e.g., 1 kW).

The electrical energy storage device of the mobile C-arm X-ray apparatus according to an embodiment includes a battery (e.g., a rapidly chargeable and energy-dense battery). In this context, a quick charging time is intended to mean charging of the battery to at least 75% of the energy storage capacity within a one hour (e.g., even considerably less than one hour). In this context, an energy-dense battery is intended to mean a battery with a comparatively high energy density (e.g., more than 60 or 70 Wh/kg).

For example, such a battery may be a lithium-ion battery. Lithium-ion batteries are characterized by a high specific energy. Lithium-ion batteries are thermally stable and are subject to only a very slight memory effect. In addition, Lithium-ion batteries are also suitable for quick charging. For instance, lithium-ion batteries battery packs are charged to 80% of their maximum energy capacity in half an hour by quick charging stations installed as "Superchargers" by the company Tesla. Such quick charging devices may be installed in hospitals at defined locations (e.g., in depots, storerooms, or in operating theaters). The mobile X-ray apparatuses may then be recharged quickly in a very short time during breaks between operations and made available again for the next operation.

The term lithium-ion battery is intended to include the following types of lithium batteries: lithium-polymer batteries, lithium-cobalt oxide batteries, lithium-titanate batteries, lithium-air batteries, lithium-manganese dioxide batteries, lithium-iron phosphate batteries, lithium-sulfur batteries and tin-sulfur-lithium ion batteries.

Other very energy-dense batteries may be used for energy storage (e.g., zinc-air batteries, sodium-air batteries and sodium-sulfur batteries).

In various embodiments, the electricity consumers of the mobile C-arm X-ray apparatus may include an electric traction unit. Such a traction unit may be used for automatic driving of the mobile X-ray apparatus. Furthermore, the electricity consumers may also include an electrically-driven actuator configured to set the position and orientation of the X-ray source and/or of other functional units for X-ray imaging. For example, the X-ray source and the X-ray detector may be configured to a specific patient position and to a desired imaging region of the patient with the aid of such an actuator.

In an embodiment of the mobile C-arm X-ray apparatus, the energy storage device includes electrically separated first and second battery packs as energy storage regions that are dischargeable separately from each other. The first battery pack is electrically connected to the X-ray source via the first electrical terminal and the second battery pack is electrically connected to the system energy supply via the second electrical terminal. By separating the two energy storage regions, independent discharge of the two energy storage regions may be achieved in a simple manner. As a result, the entire system is more robust in the event of malfunctions, inadequate maintenance and operator errors.

In another embodiment of the mobile C-arm X-ray apparatus, the energy storage device includes a battery pack that is jointly used, with the first electrical terminal providing a high supply voltage to supply the X-ray source with electrical energy and the second electrical terminal providing a low supply voltage to the system energy supply. In this way, consumers with different electrical voltages may be supplied with electrical energy from the same battery pack.

In further embodiment of the mobile C-arm X-ray apparatus, the second terminal is configured as a center tap on the energy storage device. An energy storage device may include a series circuit of a specific number of storage cells, and the entire electrical voltage of the series circuit being supplied when the electric voltage is tapped by contacts at the start and end of the series circuit. With a central tap, the entire electric voltage is not provided because one of the two contacts is not positioned at the start or at the end of the series circuit (e.g., somewhere between two storage cells in the series circuit).

In an embodiment of the mobile C-arm X-ray apparatus, the consumers (e.g., the functional units supplied with electrical energy by the system energy supply) have at least one actuator, and are configured to carry out an orbital turn, height adjustment, or length adjustment of the C-arm of the C-arm X-ray apparatus.

In addition, the mobile C-arm X-ray apparatus may sensors for orientation in the space and a navigation unit, and the navigation unit is configured to control a movement of the mobile X-ray apparatus in the space automatically (e.g., based on sensor information from the sensors).

The mobile C-arm X-ray apparatus may be electrically charged (e.g., via a charging cable at a conventional power outlet). The charging cable may also be configured to charge up on a quick charging device. Alternatively or additionally, the electrical energy storage device of the mobile C-arm X-ray apparatus may also be charged via an inductive charging interface for contactless electrical charging of the storage unit.

In another embodiment, the mobile C-arm X-ray apparatus may also be moved by hand without any problems (e.g., when the energy storage device has been drained). For example, a coupling element or a freewheel may be installed between the drive motor and the wheels that have been driven, such that when the motor is switched off, no inhibitory action is exerted on the wheels.

The C-arm X-ray apparatus may also include a power supply connection with which the C-arm X-ray apparatus may continue to work from the grid when the energy storage device has been discharged.

The mobile C-arm X-ray apparatus may additionally include a user interface with remote operation to control the mobile C-arm X-ray apparatus and a display system to display X-ray images that have been acquired. Such a user interface may include a Touch User Interface allowing for remote operation or that is docked directly on the mobile C-arm X-ray apparatus and is optionally removable. This interface may also provide the imaging system with a display for X-ray images. In addition, fixedly installed large displays may be provided for displaying the user interface and/or X-ray images that are transmitted by wireless (e.g., via WLAN), and may also be arranged in the operating theater space. Alternatively or additionally, the X-ray images may also be transmitted to any other locations for display and storage. In addition, in another embodiment, control of the mobile C-arm X-ray apparatus by a joystick or other remote control is provided.

The storage capacity of the energy storage device may be configured to operate for at least 3 to 4 hours of examination or in an operating theater. In addition, the mobile C-arm X-ray apparatus may also include a network cable for conventional sockets with which an emergency operation of the X-ray apparatus may be guaranteed when the charge status of the energy storage device is too low. A status display for displaying the current charge status of the energy storage device may also be installed on the mobile C-arm X-ray apparatus. Such a display may be provided by showing bars or a percentage figure, by a color coding or by indicating the remaining running time of the X-ray apparatus. A plurality of remaining running times (e.g., a remaining running time for the operation of the X-ray source and a remaining running time for the operation of the actuators) may also be indicated and displayed. In this context, an indication of the remaining route to be traveled by the mobile C-arm X-ray apparatus may also be provided.

DETAILED DESCRIPTION

Figure 1:
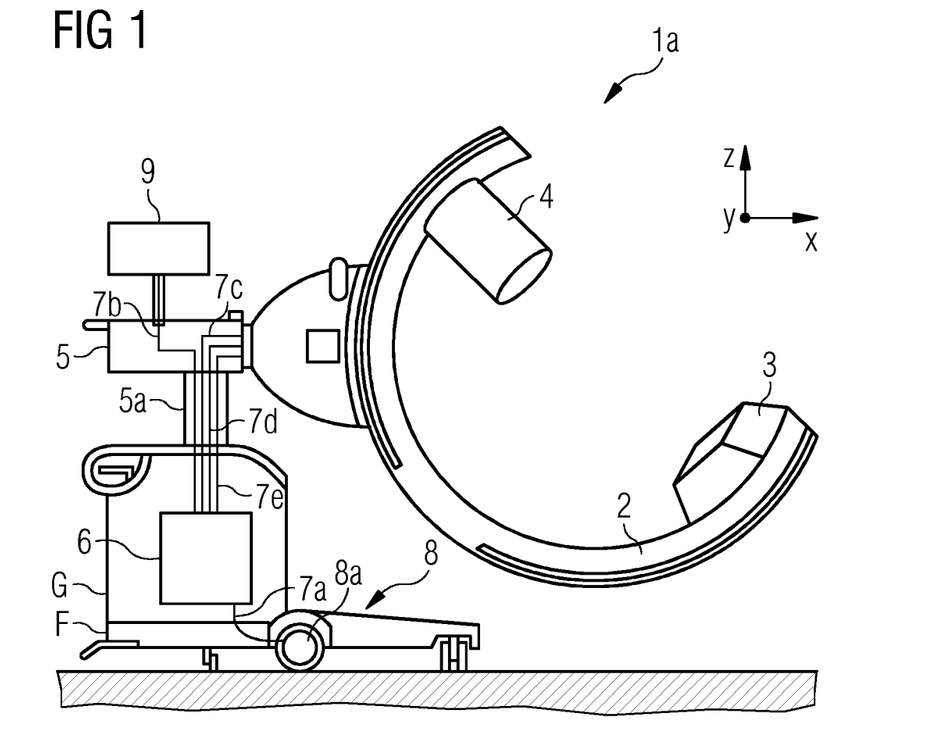
FIG. 1 shows a schematic diagram of a C-arm X-ray system according to an embodiment.

FIG. 1 shows a C-arm X-ray apparatus 1a. The C-arm X-ray apparatus 1a includes a C-arm 2. An X-ray source 3 and an X-ray detector 4 are arranged on the C-arm 2. The C-arm X-ray apparatus 1a also includes a horizontal unit 5. The horizonatal unti 5 supports the C-arm 2 and is arranged on a vertical axis 5a (e.g., corresponding to the z-axis) of the C-arm X-ray apparatus 1a.

Figure 2:
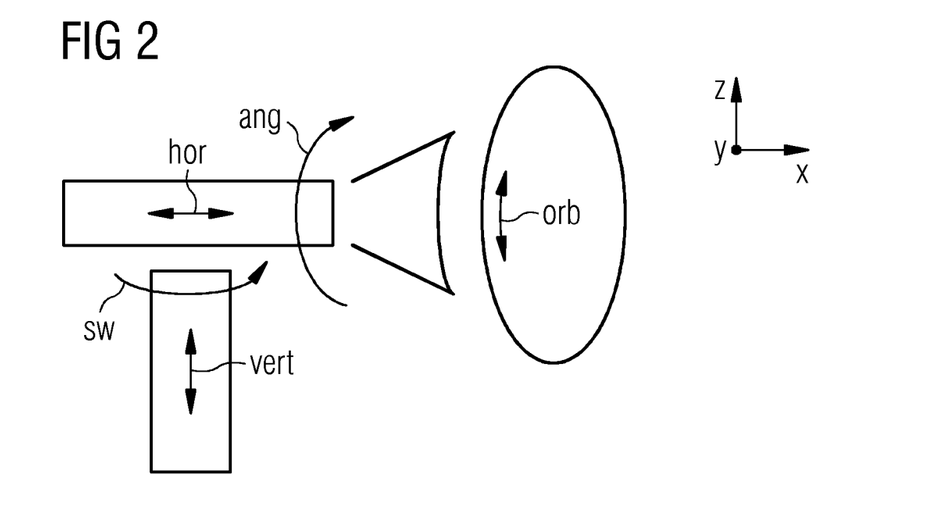
FIG. 2 shows a schematic diagram of the adjustment options of a C-arm X-ray system according to an embodiment.

FIG. 2 shows a schematic of the rotation and translation movements of the C-arm X-ray apparatus 1a. The C-arm 2 may be moved in a vertical direction vert (e.g., the z-direction). In addition, the C-arm may rotate around the z-axis (e.g., marked with "sw" in FIG. 2). In addition, the C-arm 2 may be moved in the x-direction (e.g., in the direction of the horizontal axis hor of the horizontal unit 5). Furthermore, the C-arm 2 may rotate around the horizontal axis of the horizontal unit (e.g., marked with "ang" in FIG. 2). Finally, the C-arm 2 may also be pivoted round the y-axis (e.g., orbitally rotated, marked in FIG. 2 with "orb").

As may be seen in FIG. 1, the vertical axis 5a (e.g., on which the horizontal unit 5 of the C-arm system 1a rests) is positioned on a housing G positioned in turn on a kind of chassis F. The housing G includes inter alia an energy storage unit 6 supplying both the X-ray source 3 and the remaining functional units (e.g., marked collectively as system with electrical energy). For example, the energy storage unit supplies electrical energy to a traction unit 8 including wheels 8a, and drives the wheels 8a via a traction power supply line 7a. The traction unit 8 may also include an electric motor (e.g., not shown) to drive the wheels 8a. The energy storage unit 6 additionally supplies electrical energy to a display unit 9 via a screen energy supply line 7b. In addition, the X-ray source 3 is likewise supplied with electrical energy via an X-ray source power supply line 7c. Furthermore, there are supply lines 7d, 7e for a plurality of actuators (e.g., not shown in FIG. 1). For example, the actuators are used for positioning the C-arm 2, and for the detector unit 4.

Figure 3:
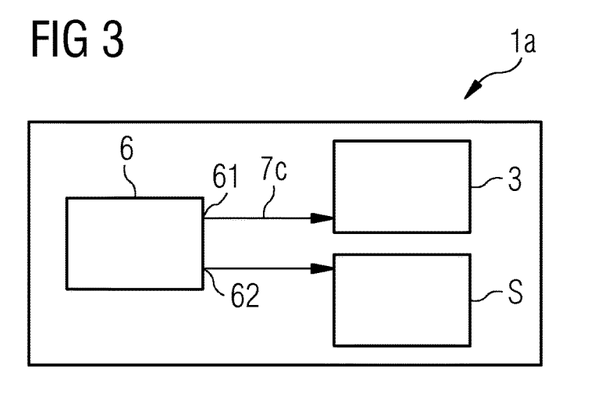
FIG. 3 shows a block circuit diagram of a C-arm X-ray system according to an embodiment.

FIG. 3 shows a block circuit diagram of the C-arm X-ray apparatus 1a from FIG. 1 schematically illustrating the design and mode of function of the energy supply to the C-arm X-ray apparatus 1a. The C-arm X-ray apparatus 1a includes an energy storage unit 6 including a lithium-ion battery pack. The cells of this lithium-ion battery pack are configured in this embodiment in the size of the form factor 18,650. However, other formats may be used for the batteries. The energy storage unit 6 is used for the power supply of all the device functions. For example, the device functions include the operation of an X-ray source 3. For example, to supply energy to the X-ray source 3, the energy storage unit 6 includes a first electrical terminal 61 with an electric voltage of 400V. Such a high electric voltage is achieved by series connection of a plurality of individual cells. In addition, the energy storage unit 6 has high-current capability. A plurality of storage cells are connected in parallel in order to generate a strong enough current to operate the X-ray source 3. With an output of the X-ray source of 25kW and an electric voltage of 400V, current with an intensity of around 62.5 amperes is provided. The first electrical terminal 61 is electrically connected to the X-ray source 3 via an electrical supply line 7c.

The energy storage unit 6 additionally includes a second electrical terminal 62 with an electric voltage of 24V (e.g., or alternatively 48V). This second electrical terminal 62 provides the energy supply to the system S. The system energy supply supplies all the electrically operated units of the C-arm X-ray apparatus 1a with the exception of the X-ray source. For example, the second electrical terminal 62 may be configured as a center tap on the lithium-ion battery pack of the energy storage device 6. At the first electrical terminal 61, the entire electric voltage available on the lithium-ion battery pack is tapped.

Figure 4:
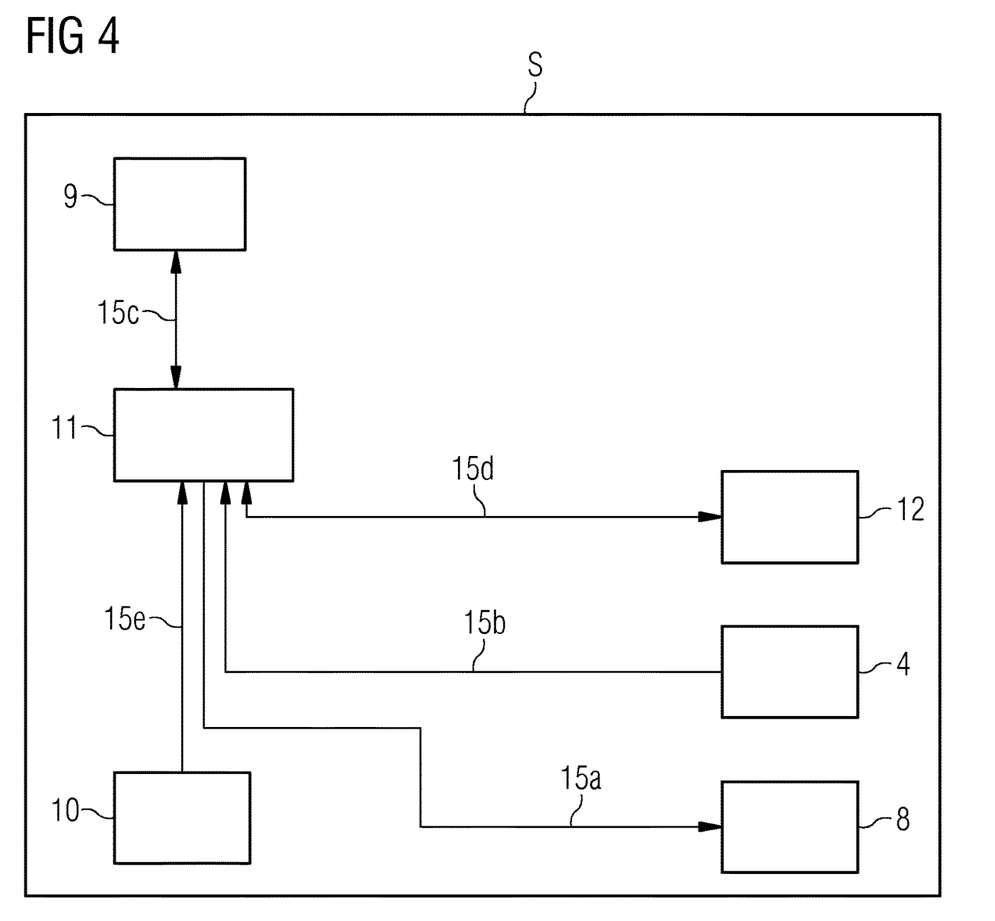
FIG. 4 shows a block circuit diagram illustrating a C-arm X-ray system according to an embodiment.
Figure 5:
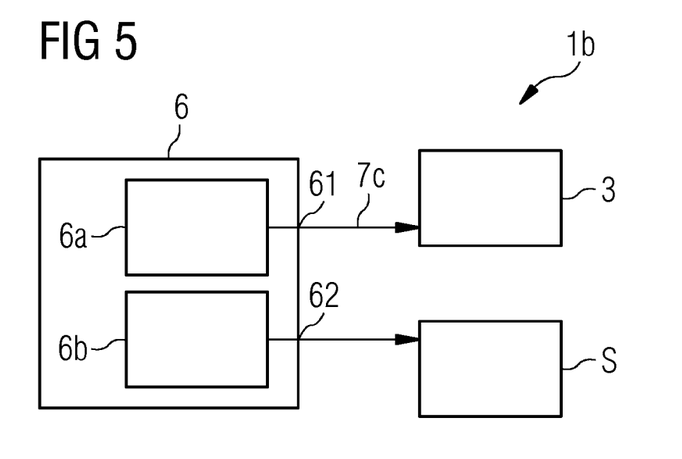
FIG. 5 shows a block circuit diagram of a C-arm X-ray system according another embodiment.
Figure 6:
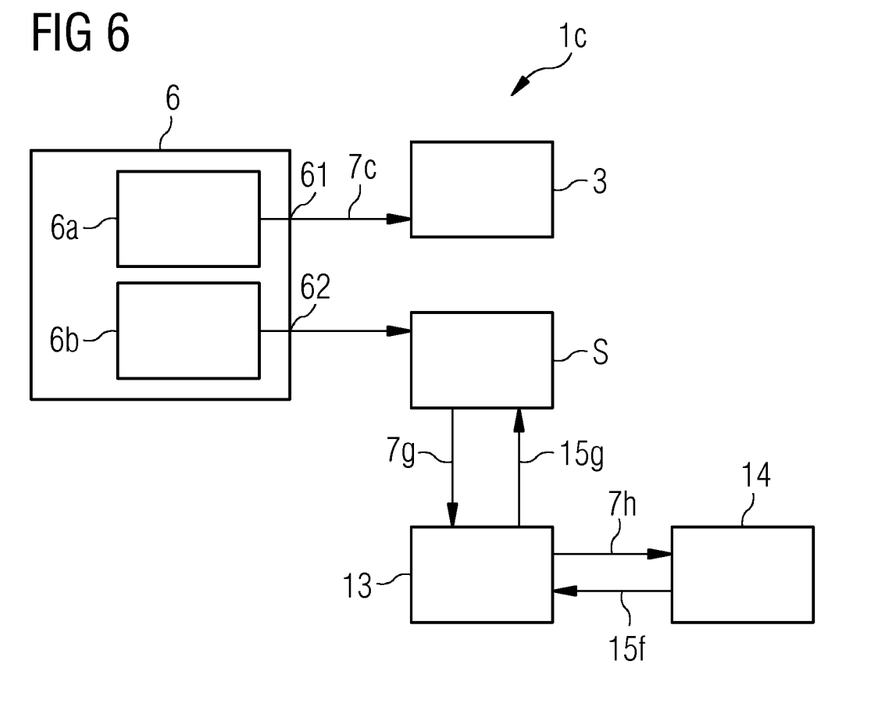
FIG. 6 shows a block circuit diagram of a C-arm X-ray system according to a further embodiment.

FIG. 4 illustrates a system S of a C-arm X-ray apparatus (e.g., part of the embodiments shown in FIGS. 3, 5 and 6. The system S includes a control unit 11 for activating the individual functional units 4, 8, 9, 10, 12 of the C-arm X-ray apparatus. The control unit 11 is connected via communications links 15a, 15b, 15c, 15d, 15e to the individual functional units 4, 8, 9, 10, 12.

The control unit 11 may be operated manually by an actuation unit 10 via a communications link 15e. The actuation unit 10 may also include a touchscreen or a tablet device that communicates via remote wireless operation with the stationary part of the actuation unit 10. Alternatively or additionally, a display unit 9 may be configured to display the image, may also be configured as a user interface. The display screen of the display unit 9 may be configured as a touchscreen (e.g., via which commands may be input and then forwarded to the control unit 11 via a communications line 15c). The display unit 9 may also be used for the graphic display of the image data acquired in an X-ray imaging procedure. The control unit 11 and the remaining functional units 4, 8, 9, 10, 12 are supplied with electrical energy via energy supply lines (e.g., see FIG. 1) by the energy storage device 6 (e.g., see FIG. 1). Furthermore, there is also a communications line between the control unit 11 and the energy storage unit 6 (e.g., not shown). For example, via this communications line, the control unit 11 receives information about the charge status of the energy storage unit 6 and may also give control commands to the energy storage unit 6 (e.g., to turn it off, or the like).

The system S includes a plurality of electrical units (e.g., a traction unit 8) that include an electric motor (e.g., not shown) to drive wheels or rollers, and also the wheels or rollers (e.g., see FIG. 1) to move the C-arm X-ray apparatus 1a. The traction unit 8 is electrically connected via a supply line (e.g., not shown) to the second electrical terminal 62. Furthermore, the traction unit 8 is connected via a communications line 15a to the control unit 11. The traction unit 8 may be activated by the communications line 15a from the control unit 11. For example, the traction unit 8 additionally includes as rollers or wheels that are known as "Omni wheels" (e.g., not shown). Omni wheels are wheels with additional rollers that are oriented orthogonally to the direction of the main wheels, and the omni-wheels allow the C-arm X-ray apparatus to move at any time into a different direction. Alternatively, "Engine Wheels" may be used. Engine Wheels are wheels with a built-in motor or a hub motor. Furthermore, the traction unit 8 may be configured such that, in a de-energized state, the C-arm X-ray apparatus 1a may be moved manually without difficulty.

In addition, actuator units 12 and the detector unit 4 are also supplied via supply lines (e.g., not shown) with electrical energy by the second electrical terminal 62 (e.g., see FIG. 3) for the orbital rotation, or height- and length adjustment of the C-arm 2. The system units are likewise activated by the control unit 11 via communications lines 15c, 15b, and may transmit data back to the control unit 11.

FIG. 5 shows a block circuit diagram of a C-arm X-ray apparatus 1b according to an embodiment. The C-arm X-ray apparatus 1b includes the C-arm X-ray apparatus 1a discussed above and a plurality of functional units jointly denoted by the term "System" S. For example, the system S includes an actuation unit 10, a control unit 11, a display unit 9, and a plurality of additional functional units (e.g., a traction unit 8, a detector unit 4 and a plurality of actuators 12) (e.g., see FIG. 4). In addition, the C-arm X-ray apparatus 1b also includes an energy storage unit 6. Unlike the energy storage unit of the C-arm X-ray apparatus 1a discussed above, the energy storage unit 6 is divided into two battery packs 6a, 6b that are electrically separated from each other. A first battery pack 6a provides the energy supply to the X-ray source 3 and a second battery pack 6b to the system energy supply (e.g., the energy supply to all the other functional units 4, 8, 9, 10, 11, 12 combined in FIG. 5 with the reference sign "S"). The complete separation of the two battery packs 6a, 6b provides that, after the two battery packs have been discharged up to an allowed minimum value, the technical functions of the functional units assigned to the other battery pack continue to be guaranteed. For example, when a complete discharge up to a permitted minimum value of the first battery pack 6a by the X-ray source 3 occurs, the C-arm X-ray apparatus 1b may continue to remain usable and movable.

FIG. 6 shows a block circuit diagram of the C-arm X-ray apparatus 1c according to another embodiment. Just like the C-arm X-ray apparatus 1b discussed above, the C-arm X-ray apparatus 1c likewise includes an X-ray source 3 and functional units combined in the system S (e.g., a traction unit 8, a detector unit 4, and a plurality of actuators 12) (e.g., see FIG. 4). In addition, the C-arm X-ray apparatus 1c also includes an energy storage unit 6 including two battery packs 6a, 6b that are electrically separate from each other. In addition, the C-arm X-ray apparatus 1c includes a navigation unit 13 and a sensor unit 14. The navigation unit 13 is supplied with electrical energy by an electrical supply line 7g. The sensor unit 14 is also supplied with electrical energy via an electrical supply line 7h. For example, the sensor unit 14 includes a sensor system (e.g., laser scanners or cameras) for automatic orientation in the space. The sensor information acquired is transmitted via a communications line 15f to the navigation unit 13 for carrying out a position determination from this information. The information on the current position of the C-arm X-ray apparatus 1c is transmitted via a communications line 15g to the control unit 11 (e.g., see FIG. 4) of the system S. Based on the position information that has been acquired, the control unit 11 controls the traction unit 8 and the actuators 12 (e.g., see FIG. 1, FIG. 4) to drive to specified areas or positions (e.g., an examination position or a parking position, or to carry out autonomous docking alongside a table or a charging station). The sensor system of the sensor unit 14 that is described may also be used to avoid a collision. For example, for this purpose capacitive approximation sensors or mechanical protection elements may be provided, serving first as impact protection and additionally providing information on obstacles that are approaching or have been touched.

Finally, it is once again pointed out that the apparatuses described in the aforementioned merely relate to embodiments of the invention and that the embodiments may be varied by a person skilled in the art without departing from the scope of the invention insofar as it is set out in the claims. Therefore, the embodiments have been described in the first instance with reference to a system for acquiring medical imaging data. The embodiment is not restricted to an application in the medical field, but the embodiment may also be applied to the acquisition of images for other purposes. For the sake of completeness, it is also pointed out that the use of the indefinite article "a" or "an" does not preclude the relevant features from being present in plurality. Likewise the term "unit" does not preclude this from including a plurality of components that may optionally also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A mobile C-arm X-ray apparatus comprising:
    an electrically operated X-ray source; and
    an electrical energy storage device comprising a high current-capable battery, the high current-capable battery comprising a first electrical terminal configured to be electrically connected to the electrically operated X-ray source and a second electrical terminal,
    wherein a system energy supply is configured to supply a detector unit with electrical energy via the second electrical terminal, and
    wherein the system energy supply is configured to supply all electrical consumers of the mobile C-arm X-ray apparatus, with exception of the electrically operated X-ray source, with electrical energy.

2. The mobile C-arm X-ray apparatus of claim 1, wherein the electrical energy storage device comprises at least two energy storage regions,
    wherein a first energy storage region of the at least two energy storage regions is configured to be electrically connected to the first electrical terminal and a second energy storage region of the at least two energy storage regions is configured to be electrically connected to the second electrical terminal, and
    wherein the first and the second energy storage regions are configured to be dischargeable independently from each other.

3. The mobile C-arm X-ray apparatus of claim 2, wherein the electrical energy storage device comprises first and second battery packs as energy storage regions, wherein the first and second battery packs are electrically separate and dischargeable independently from each other.

4. The mobile C-arm X-ray apparatus of claim 1, wherein the electrical energy storage device comprises a quick-chargeable and energy-dense battery.

5. The mobile C-arm X-ray apparatus of claim 1, wherein the electrical energy storage device comprises an Li-ion battery.

6. The mobile C-arm X-ray apparatus of claim 1, wherein the electrical consumers comprise an electric traction unit, an electrically driven actuator configured for adjusting a position and an orientation of the electrically operated X-ray source, other functional units for X-ray imaging, or a combination thereof.

7. The mobile C-arm X-ray apparatus of claim 1, wherein the electrical energy storage device comprises a common battery pack, wherein the first electrical terminal is configured to provide a high supply voltage to supply the electrically operated X-ray source with electrical energy and the second electrical terminal is configured to provide a low supply voltage for the system energy supply.

8. The mobile C-arm X-ray apparatus of claim 7, wherein the second electrical terminal is configured as a center tap on the electrical energy storage device.

9. The mobile C-arm X-ray apparatus of claim 1, wherein the electrical consumers comprise at least one actuator configured to carry out an orbital rotation, height or length adjustment of a C-arm of the mobile C-arm X-ray apparatus.

10. The mobile C-arm X-ray apparatus of claim 1, further comprising:
    a sensor system for orientation in a space; and
    a navigation unit configured to automatically control a movement of the mobile C-arm X-ray apparatus in the space based on sensor information from the sensor system.

11. The mobile C-arm X-ray apparatus of claim 1, wherein the mobile C-arm X-ray apparatus is configured to be moveable by hand when the electrical energy storage device has been discharged.

12. The mobile C-arm X-ray apparatus of claim 1, further comprising:
    a user interface, wherein the user interface comprises:
        a remote operation configured to control the mobile C-arm X-ray apparatus; and
        a display system configured to display X-ray images that have been acquired and for system control.

13. A mobile C-arm X-ray apparatus comprising:
    an electrically operated X-ray source; and
    an electrical energy storage device comprising a high current-capable battery, the high current-capable battery comprising a first electrical terminal configured to be electrically connected to the electrically operated X-ray source and a second electrical terminal,
    wherein a system energy supply is configured to supply a detector unit with electrical energy via the second electrical terminal, and
    wherein the electrical energy storage device comprises an inductive charging interface for contactless electrical charging of the electrical energy storage device.

14. A method for operating a mobile C-arm X-ray apparatus, the method comprising:
    providing an electrically operated X-ray source; and
    providing an electrical energy storage device comprising a high current-capable battery, the high current-capable battery comprising a first electrical terminal configured to be electrically connected to the electrically operated X-ray source and a second electrical terminal, wherein a system energy supply is configured to supply a detector unit with electrical energy via the second electrical terminal;
    supplying the electrically operated X-ray source with electrical energy from the electrical energy storage device via the first electrical terminal; and
    supplying, via the system energy supply via the second electrical terminal of the electrical energy storage device, all electrical consumers of the mobile C-arm X-ray apparatus, with exception of the electrically operated X-ray source, with electrical energy.

* * * * *